United States Patent
He et al.

(10) Patent No.: US 10,669,266 B2
(45) Date of Patent: Jun. 2, 2020

(54) OXADIAZOLE INHIBITORS OF HIPK2 FOR TREATING KIDNEY FIBROSIS

(71) Applicants: ICAHN SCHOOL OF MEDICINE AT MOUNT SINAI, New York, NY (US); UNIVERSITY OF KANSAS, Lawrence, KS (US)

(72) Inventors: John Cijiang He, New York, NY (US); Ruijie Liu, New York, NY (US); Bhaskar Das, Kansas City, KS (US); Wenzhen Xiao, New York, NY (US); Zhengzhe Li, New York, NY (US); Kyung Lee, New York, NY (US)

(73) Assignees: ICAHN SCHOOL OF MEDICINE AT MOUNT SINAI, New York, NY (US); UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 16/473,878

(22) PCT Filed: Jan. 5, 2018

(86) PCT No.: PCT/US2018/012512
§ 371 (c)(1),
(2) Date: Jun. 26, 2019

(87) PCT Pub. No.: WO2018/129274
PCT Pub. Date: Jul. 12, 2018

(65) Prior Publication Data
US 2019/0352292 A1    Nov. 21, 2019

Related U.S. Application Data

(60) Provisional application No. 62/445,461, filed on Jan. 12, 2017, provisional application No. 62/443,370, filed on Jan. 6, 2017.

(51) Int. Cl.
| | | |
|---|---|---|
| C07D 271/04 | (2006.01) | |
| C07D 271/06 | (2006.01) | |
| C07D 271/08 | (2006.01) | |
| C07D 271/107 | (2006.01) | |
| C07D 413/04 | (2006.01) | |
| C07F 5/04 | (2006.01) | |
| A61P 13/12 | (2006.01) | |
| C07D 413/14 | (2006.01) | |
| C07F 5/02 | (2006.01) | |
| C12N 9/99 | (2006.01) | |

(52) U.S. Cl.
CPC ........... *C07D 413/04* (2013.01); *A61P 13/12* (2018.01); *C07D 271/04* (2013.01); *C07D 271/06* (2013.01); *C07D 271/08* (2013.01); *C07D 271/107* (2013.01); *C07D 413/14* (2013.01); *C07F 5/02* (2013.01); *C07F 5/025* (2013.01); *C07F 5/04* (2013.01); *C12N 9/99* (2013.01)

(58) Field of Classification Search
CPC .. C07D 271/04; C07D 271/06; C07D 271/08; C07D 271/107; C07D 413/04; C07F 5/04; C07F 5/025
See application file for complete search history.

(56) References Cited

U.S. PATENT DOCUMENTS

| | | |
|---|---|---|
| 2006/0040253 A1 | 2/2006 | Roberts et al. |
| 2009/0054658 A1 | 2/2009 | Uehira |
| 2014/0088191 A1 | 3/2014 | Zhuang |
| 2017/0253873 A1 | 9/2017 | Leof et al. |

FOREIGN PATENT DOCUMENTS

WO    2011106689 A1    9/2011

OTHER PUBLICATIONS

Naraya et al., Archiv der Pharmazie (Weinheim, Germany) (2005), 338(8), pp. 373-377. (Year: 2005).*
Sung et al., Liquid Crystals (2004), 31(6), pp. 831-840. (Year: 2004).*
Andersen et al., Advanced Synthesis & Catalysis, 2014, 356(14-15), pp. 3074-3082. (Year: 2014).*
Chemical Abstracts Registry No. 1654021-98-3, 2015. (Year: 2015).*
International Search Report and Written Opinion issued in PCT Application No. PCT/US2018/012512, dated May 30, 2018, 10 pages.
Ruijie Liu et al, "A Novel Inhibitor of Homeodomain Interacting Protein Kinase 2 Mitigates Kidney Fibrosis through Inhibition of the TGF-B1/Smad3 Pathway," Journal of the American Society of Nephrology, Feb. 20, 2017, vol. 28, No. 7, pp. 2133-2143.

* cited by examiner

*Primary Examiner* — Laura L Stockton
(74) *Attorney, Agent, or Firm* — Heslin Rothenberg Farley & Mesiti, P.C.

(57) ABSTRACT

Compounds that are selective inhibitors of Smad3 activation are disclosed. The compounds have the following structure:

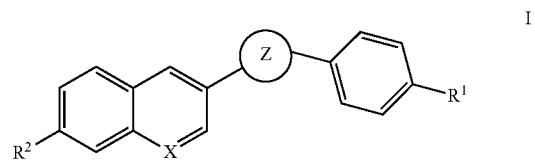

in which Z is an oxadiazole. The compounds disclosed are useful in treatment of fibrotic disease, particularly renal fibrosis, and similar diseases associated with the dysregulation of the HIPK2/Smad3 signaling pathway.

21 Claims, No Drawings
Specification includes a Sequence Listing.

OXADIAZOLE INHIBITORS OF HIPK2 FOR TREATING KIDNEY FIBROSIS

CROSS-REFERENCE TO RELATED APPLICATIONS

This application is the National Phase filing under 35 U.S.C. § 371 of International Application No.: PCT/US2018/012512, filed on Jan. 5, 2018, and published on Jul. 12, 2018 as WO2018/129274, which claims priority from U.S. provisional application 62/443,370, filed Jan. 6, 2017, and from U.S. provisional application 62/445, 461, filed Jan. 12, 2017. The entire contents of both all of which are incorporated herein by reference.

STATEMENT REGARDING FEDERALLY SPONSORED RESEARCH OR DEVELOPMENT

This invention was made with government support under 1R01DK088541-01A1 awarded by National Institutes of Health. The government has certain rights in the invention.

FIELD OF THE INVENTION

This invention relates to oxadiazole-based chemical inhibitors of homeodomain interacting protein kinase 2 (HIPK2). The compounds disclosed are useful in treatment of kidney diseases.

BACKGROUND

Fibrosis is characterized by excessive production and accumulation of extracellular matrix proteins, which leads to progressive loss of tissue function and eventual organ failure. Chronic kidney diseases, irrespective of primary insults, are usually accompanied by kidney interstitial fibrosis. Therapeutic strategy for chronic kidney disease, in order to halt decline of kidney function, requires not only removal of the causal factors, such as hyperglycemia, hypertension, and HIV infection, but also anti-fibrosis therapy to restore the normal kidney structure and function.

Transforming growth factor-β1 (TGF-β1) has been identified to be the most important pro-fibrogenic factor for kidney disease. TGF-β1 binds to type II TGF-β receptor, allowing its dimerization with type I TGF-β receptor and leading to phosphorylation of Smad2 and Smad3. Phosphorylated Smad3 relocates into nuclei, thereby binds to Smad binding element in promoter and activating the transcription of the target genes including pro-fibrotic genes such as collagen I, fibronectin, and alpha-smooth muscle actin (α-SMA). It is known that Smad3 is highly activated in fibrotic kidney and that knockout of Smad3 attenuates kidney fibrosis in animal models of kidney disease. Blockade of TGF-β1/Smad3 pathway therefore provides a therapeutic strategy for kidney fibrosis.

BRIEF SUMMARY OF THE INVENTION

It has now been found that certain compounds described below selectively inhibit Smad3 activation.

In one aspect, the invention relates to compounds of general formula I

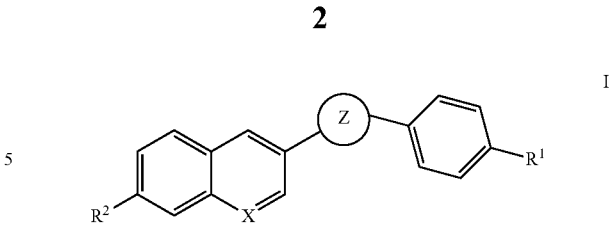

wherein
Z is an oxadiazole;
X is chosen from N and CH;
$R^1$ and $R^2$ are chosen independently from —($C_1$-$C_8$)hydrocarbyl, OH, —O($C_1$-$C_8$)hydrocarbyl, halogen, nitro, ($C_1$-$C_3$)alkylamino, ($C_1$-$C_3$)dialkylamino, ($C_1$-$C_3$)acylamino, ($C_1$-$C_3$)alkylsulfonyl, ($C_1$-$C_3$)alkylthio, ($C_1$-$C_3$)haloalkyl, ($C_1$-$C_3$)haloalkoxy, ($C_1$-$C_3$)haloalkylthio, —COOH, —C(=O)O($C_1$-$C_3$)alkyl, —B($OR^3$)$_2$, and —$BF_3K$; and
$R^3$ is H or ($C_1$-$C_8$)hydrocarbyl; or ($OR^3$)$_2$, taken together with the boron to which they are attached form a dioxaborolane or dioxaborinane ring optionally substituted with from one to four ($C_1$-$C_8$)hydrocarbyl.

In another aspect, the invention relates to pharmaceutical compositions comprising a pharmaceutically acceptable carrier and a compound of formula I.

In another aspect, the invention relates to methods for inhibiting the interaction of homeodomain interacting protein kinase 2 (HIPK2) with Smad3. The method comprises bringing HIPK2 into contact with a compound of formula I.

In another aspect, the invention relates to a method for treating a fibrotic disease comprising administering a compound of formula I.

DETAILED DESCRIPTION OF THE INVENTION

In one aspect, the invention relates to compounds having general formula I as described above:

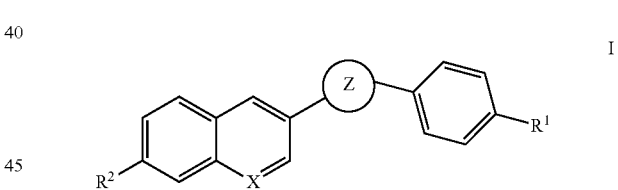

In some embodiments of formula I, Z is a 3,5-disubstituted [1,2,4]oxadiazole.

In some embodiments of formula I, $R^1$ is chosen from halogen, —COOH, —C(=O)O($C_1$-$C_3$)alkyl, —B($OR^3$)$_2$, and —$BF_3K$. In some embodiments, $R^1$ may be bromine, COOEt, or —$BF_3K$.

In some embodiments of formula I, $R^2$ is chosen from halogen, ($C_1$-$C_3$)haloalkyl, —O($C_1$-$C_3$)alkyl, —B($OR^3$)$_2$, and —$BF_3K$. In some embodiments, $R^2$ may be bromine, $OCH_3$, or —$CF_3$.

In some embodiments of formula I, X is nitrogen.

For convenience and clarity, certain terms employed in the specification, examples, and claims are described herein. Substituents R″ are generally defined when introduced and retain that definition throughout the specification and in all independent claims.

Unless otherwise specified, alkyl (or alkylene) is intended to include linear or branched saturated hydrocarbon structures and combinations thereof. Alkyl refers to alkyl groups of from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Hydrocarbon or hydrocarbyl refer to any substituent comprised of hydrogen and carbon as the only elemental constituents. Aliphatic hydrocarbons or hydrocarbyls are hydrocarbons or hydrocarbyls that are not aromatic; they may be saturated or unsaturated, cyclic, linear or branched. Examples of aliphatic hydrocarbons or hydrocarbyls include isopropyl, 2-butenyl, 2-butynyl, cyclopentyl, norbornyl, etc. Aromatic hydrocarbons or hydrocarbyls include benzene (phenyl), naphthalene (naphthyl), anthracene, etc.

Hydrocarbyloxy refers to groups of from 1 to 20 carbon atoms, preferably 1 to 10 carbon atoms, more preferably 1 to 6 carbon atoms attached to the parent structure through an oxygen. Alkoxy is a subset of hydrocarbyloxy and includes groups of a straight or branched configuration. Examples include methoxy, ethoxy, propoxy, isopropoxy and the like. Lower-alkoxy refers to groups containing one to four carbons.

In some embodiments, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine. Such compounds (e.g. perfluoroalkyl) fall within the class of "halohydrocarbon" and "haloalkyl".

The term "halogen" means fluorine, chlorine, bromine or iodine atoms.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons. The double bonded oxygen, when referred to as a substituent itself is called "oxo".

As used herein, and as would be understood by the person of skill in the art, the recitation of "a compound"—unless expressly further limited—is intended to include salts of that compound. Thus, for example, the recitation "a compound of formula I" as depicted above wherein X is N, would include salts of the quinoline:

Similarly, compounds which incorporate a substituent COOH, would include salts in which the substituent is COO– M+, wherein M is any counterion, and compounds carrying an amino substituent, $NH_2$, would also include salts in which the substituent is $NH_3$+ X–, wherein X is any counterion. In a particular embodiment, the term "compound of formula I" refers to the compound or a pharmaceutically acceptable salt thereof.

The term "pharmaceutically acceptable salt" refers to salts whose counter ion derives from pharmaceutically acceptable non-toxic acids and bases. Suitable pharmaceutically acceptable acids for salts of the compounds of the present invention include, for example, acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. Suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

A "therapeutically effective amount" means the amount that, when administered to a subject for treating a disorder or condition, is sufficient to effect such treatment.

It will be recognized that the compounds of this invention can exist in radiolabeled form, i.e., the compounds may contain one or more atoms containing an atomic mass or mass number different from the atomic mass or mass number usually found in nature. Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include $^{2}H$, $^{3}H$, $^{11}C$, $^{13}C$, $^{14}C$, $^{15}N$, $^{35}S$, $^{18}F$, $^{36}Cl$, $^{125}I$, $^{124}I$, and $^{131}I$ respectively. Compounds that contain those radioisotopes and/or other radioisotopes of other atoms are within the scope of this invention. Tritiated, i.e. $^{3}H$, and carbon-14, i.e., $^{14}C$, radioisotopes are particularly preferred for their ease in preparation and detectability. Compounds that contain isotopes $^{11}C$, $^{13}N$, $^{15}O$, $^{124}I$ and $^{18}F$ are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Persons of skill will readily appreciate that compounds described herein, when appropriately labeled as described above, can be employed in a method of identifying (i.e. labeling) HIPK2. Using methods well known to persons of skill in the art, HIPK2 can be localized in tissues, cells and organelles.

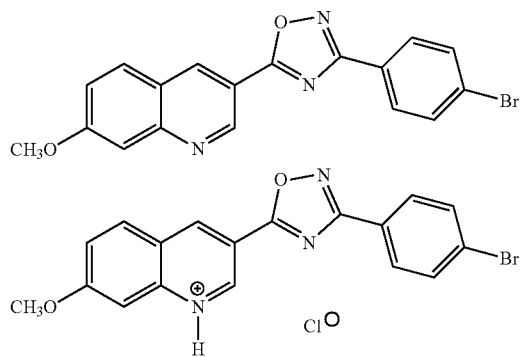

While it may be possible for the compounds of formula I to be administered as the raw chemical, it is preferable to present them as a pharmaceutical composition. According to a further aspect, the present invention provides a pharmaceutical composition comprising a compound of formula I, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

Formulations include those suitable for oral, parenteral (including subcutaneous, intradermal, intramuscular, intravenous and intraarticular), rectal and topical (including dermal, buccal, sublingual and intraocular) administration. The compounds are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. The formulations may conveniently be presented in unit dosage form and may be prepared by any of the methods well known in the art of pharmacy. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

It should be understood that in addition to the ingredients particularly mentioned above, the formulations of this invention may include other agents conventional in the art having regard to the type of formulation in question, for example those suitable for oral administration may include flavoring agents.

As used herein, "treatment" or "treating," or "palliating" or "ameliorating" are used interchangeably herein. These terms refers to an approach for obtaining a therapeutic benefit in the form of eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. The compositions may be administered to a patient at risk of developing a particular disease, or to a patient reporting one or more of the physiological symptoms of a disease, even though a diagnosis of this disease may not have been made.

Terminology related to "protecting", "deprotecting" and "protected" functionalities may occur in this application. Such terminology is well understood by persons of skill in the art and is used in the context of processes that involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the *Journal of Organic Chemistry*. The list, which is typically presented in a table entitled "Standard List of Abbreviations", is incorporated herein by reference.

In general, the compounds of the present invention may be prepared by the methods illustrated in the general reaction scheme as, for example, described below, or by modifications thereof, using readily available starting materials, reagents and conventional synthesis procedures. In these reactions, it is also possible to make use of variants that are in themselves known, but are not mentioned here. The starting materials are either commercially available, synthesized as described in the examples or may be obtained by the methods well known to persons of skill in the art.

The appropriate quinoline carboxylic acids, which are the building blocks for one portion of the molecule, may be synthesized from the corresponding anilines by the route shown in Scheme 1

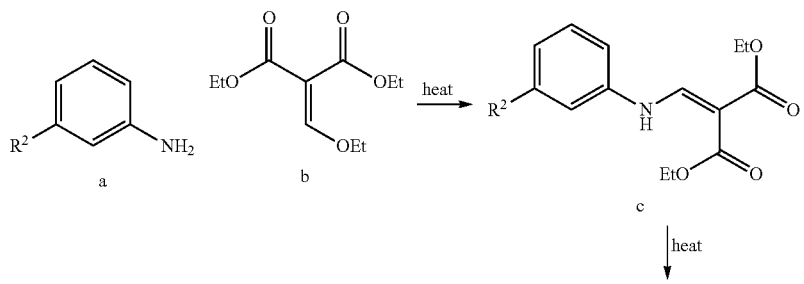

-continued

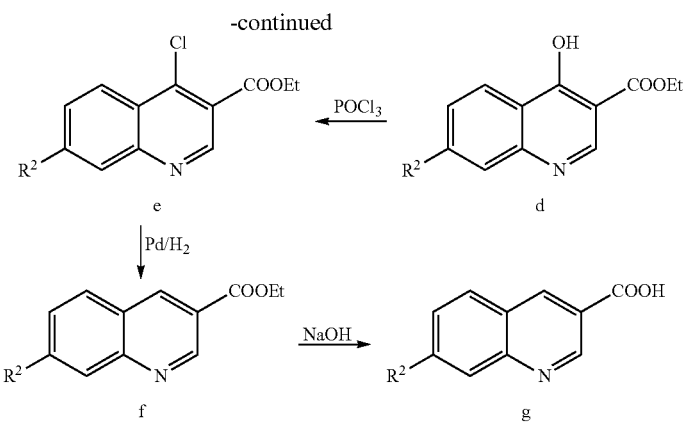

The appropriate amidoximes, which are the building blocks for another portion of the molecule, may be synthesized from the corresponding nitriles by the method of Scheme 2:

Scheme 2

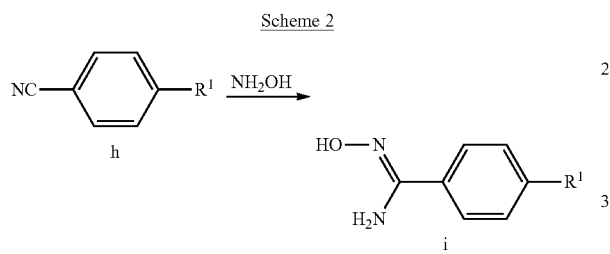

The quinoline carboxylic acids g are then reacted with the amidoximes i in the presence of carbonyl diimidazole (CDI) to provide the [1,2,4]oxadiazoles as shown in Scheme 3:

Scheme 3

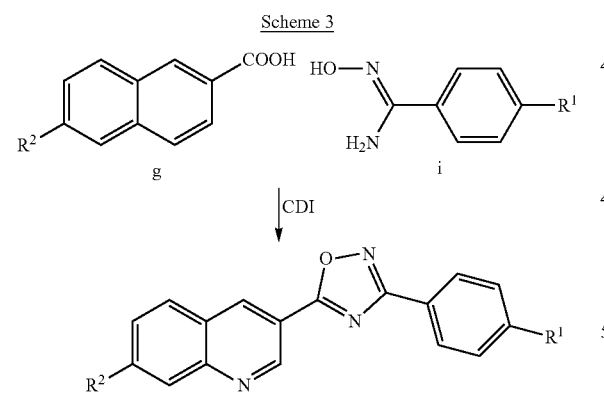

Oxadiazoles of formula I in which X is CH may be made in analogous fashion from the corresponding naphthalenecarboxylic acids.

Several methods are well known for the synthesis of 1,3,4-oxadiazoles. The commonly used synthetic route for 1,3,4-oxadiazoles includes reactions of acid hydrazides (or hydrazine) with acid chlorides/carboxylic acids and direct cyclization of diacylhydrazines using a variety of dehydrating agents such as phosphorous oxychloride, thionyl chloride, phosphorous pentaoxide, triflic anhydride, or polyphosphoric acid.

Scheme 4

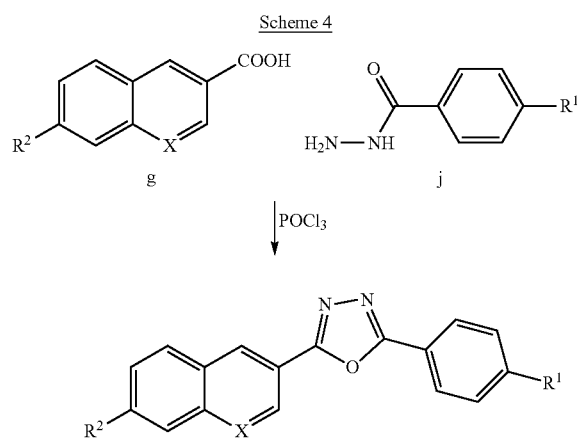

Specific examples of compounds of the present invention made via the schemes above include:

| Example # | Structure |
| --- | --- |
| 1 | ![structure] |

-continued
| Example # | Structure |
|---|---|
| 2 | 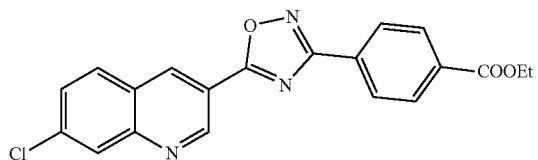 [SMILES: CCOC(=O)c1ccc(-c2noc(-c3cnc4cc(Cl)ccc4c3)n2)cc1] |
| 3 | 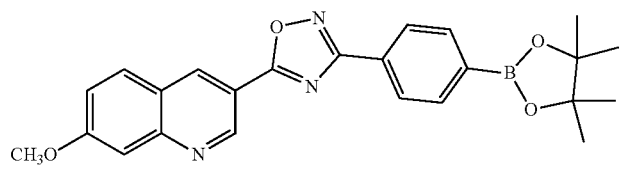 |
| 4 | 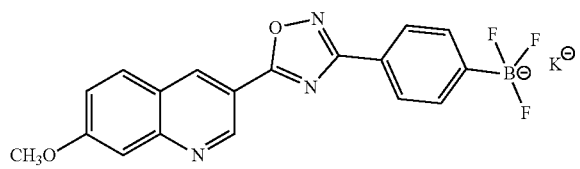 |
| 5 | 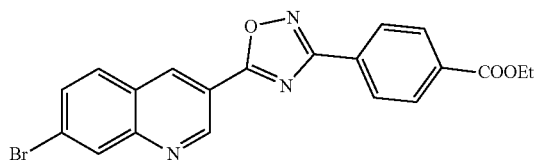 |
| 6 | 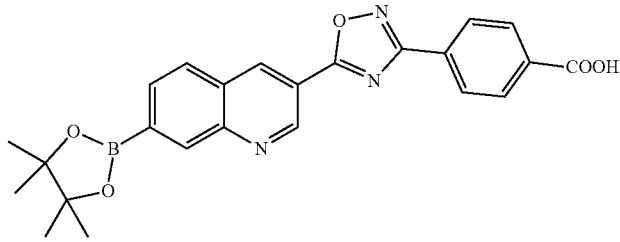 [SMILES: CC1(C)OB(c2ccc3cc(-c4nc(-c5ccc(C(=O)O)cc5)no4)cnc3c2)OC1(C)C] |
| 7 | 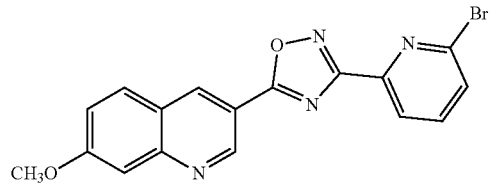 |
| 8 | 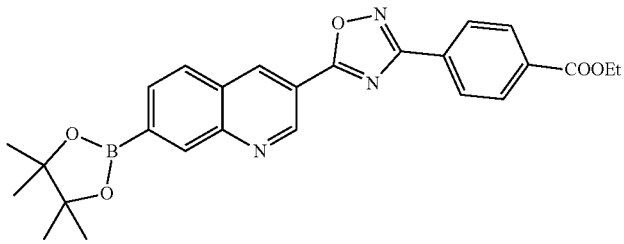 [SMILES: CCOC(=O)c1ccc(-c2noc(-c3cnc4cc(B5OC(C)(C)C(C)(C)O5)ccc4c3)n2)cc1] |

-continued

| Example # | Structure |
|---|---|
| 9 | quinoline with 7-B(OH)₂ substituent, connected at 3-position to a 1,2,4-oxadiazole bearing a 4-carboxyphenyl group |

Representative syntheses follow:

Example 1. 3-(4-Bromophenyl)-5-(7-methoxyquinolin-3-yl)-1,2,4-oxadiazole

Diethyl 2-(((3-methoxyphenyl)amino)methylene)malonate m-Anisidine (3.5 g, 0.028 mol, 3.18 mL) and diethyl ethoxymethylenemalonate (7.4 g, 6.915 mL, 0.034 mol) were mixed and heated to 130° C. for 1 hr. Cooling to room temperature resulted in yellow oil that was placed in an ice bath left in refrigerator for 2 hr. The solid that formed was crystallized with hexane to give product (5.2 g, 62.5%) as white feathery solid. $\delta_H$ (400 MHz; CDCl₃) 1.30 (3H, t, J=8.0 Hz), 1.35 (3H, t, J=8.0 Hz), 3.82 (3H, s), 4.23 (2H, q, J=8.0 Hz), 4.28 (2H, q, J=8.0 Hz), 6.65 (1H, t, J=4.0 Hz), 6.72 (2H, m), 7.27 (1H, q, J=8.0 Hz), 8.50 (1H, d, J=12.0 Hz, H-7), 10.97 (1H, d, J=12.0 Hz).

Ethyl 4-hydroxy-7-methoxyquinoline-3-carboxylate

Diethyl 2-(((3-methoxyphenyl)amino)methylene)malonate (1.48 g, 5.05 mmol) was added to already refluxing (265° C.) phenyl ether (10 mL). The mixture was left to reflux for 1 hr. and then cooled to room temperature. The solid that formed was filtered and washed thoroughly with hexane to give product (0.7 g, 57%) as a white powder. $\delta_H$ (400 MHz; d-DMSO) 1.29 (3H, t, J=8.0 Hz), 3.86 (3H, s) 4.20 (2H, q, J=8.0 Hz), 7.01 (2H, m), 8.05 (1H, d, J=8.0 Hz), 8.49 (1H, s), 12.11 (1H, br, s).

Ethyl 4-chloro-7-methoxyquinoline-3-carboxylate

Ethyl 4-hydroxy-7-methoxyquinoline-3-carboxylate (0.68 g, 2.75 mmol) was added to phosphorus oxychloride (2 mL) and heated at 140° C. for an hour. The mixture was then poured onto ice, neutralized with 1M NaOH resulting in a solid that was filtered, washed with water and dried to afforded product (0.50 g, 68%) as yellowish solid. $\delta_H$ (400 MHz; CDCl₃) 1.46 (3H, t, J=4.0 Hz), 3.99 (3H, s), 4.48 (2H, q, J=8.0 Hz), 7.33 (1H, m), 7.44 (1H, d, J=2.8 Hz), 8.30 (1H, d, J=8.0 Hz), 9.17 (1H, s). $\delta_C$ (100 MHz; CDCl₃) 14.2, 55.8, 61.8, 107.6, 120.7, 121.5, 126.7, 143.4, 150.9, 151.7.

Ethyl 7-methoxyquinoline-3-carboxylate hydrochloride

To a stirred suspension of ethyl 4-chloro-7-methoxyquinoline-3-carboxylate (1.99 mmol, 0.5 g) in EtOH (5 mL) under inert atmosphere was added Pd(OH)₂ 10% (0.05 g). The mixture was stirred at r.t. under H₂ for 2 hr. The mixture was filtered and the solvent was evaporated under vacuum to give the product (0.41 g, 82%). δH (400 MHz; CDCl₃) 1.47 (3H, t, J=4.0 Hz), 4.1 (3H, s), 4.53 (2H, br q), 7.47 (1H, br d), 8.01 (2H, br s), 9.13 (1H, s), 9.46 (1H, br s).

7-Methoxyquinoline-3-carboxylic acid

Ethyl 7-methoxyquinoline-3-carboxylate hydrochloride (1.5 g, 5.5 mmol) was hydrolyzed in 10 mL EtOH and 2M sodium hydroxide. The reaction mixture was stirred overnight. After concentration under vacuum, the mixture was acidified with 1M HCl. The resultant solid was filtered, washed with water and dried to get a beige solid (1.05 g, 89%) was obtained as a white solid. $\delta_H$(400 MHz; d-DMSO) 3.97 (3H, s), 7.35 (1H, d, J=8.0 Hz), 7.47 (1H, s), 8.10 (1H, d, J=12.0 Hz), 8.87 (1H, s), 9.24 (1H, s). $\delta_C$(100 MHz; d-DMSO) 55.7, 107.2, 120.1, 121.6, 121.8, 130.6, 137.8, 150.2, 151.0, 162.0, 166.5.

3-(4-Bromophenyl)-5-(7-methoxyquinolin-3-yl)-1,2,4-oxadiazole (Example 1)

7-Methoxyquinoline-3-carboxylic acid (2.0 mmol, 0.4 g) and CDI (2.4 mmol, 0.39 g) were dissolved in 18 mL DMF and stirred at r.t. for 30 min. (E)-4-bromo-N'-hydroxybenzimidamide (2.4 mmol, 0.54 g) was added and the reaction mixture was heated under reflux for 24 h. The mixture was poured into water (40 mL) extracted with EtOAc (3×20 mL) and the combined layer were dried over Na₂SO₄, filtered and concentrated in vacuo. The crude product was purified by silica gel column chromatography to give the oxadiazole product as a white solid (0.3 g). 1H NMR (400 MHz, CDCl₃): 9.57 (1H, s), 8.89 (1H, s), 8.09 (2H, d, J=8 Hz), 7.87 (1H, d, J=12 Hz), 7.68 (2H, d, J=8 Hz), 7.51 (1H, s), 7.33 (1H, dd, J₁=8 Hz, J₂=4 Hz), 4.01 (3H, s). 13C NMR (100 MHz, CDCl₃): 174.4, 168.3, 162.9. 151.7, 148.6, 135.9, 129.9, 129.0, 125.6, 122.1, 121.4, 115.3, 107.7, 55.8.

Example 3. 5-(7-methoxyquinolin-3-yl)-3-(4-(4,4,5,5-tetramethyl-1,3,2-dioxaborolan-2-yl)phenyl)-1,2,4-oxadiazole The compound of Example 1 (0.52 mmol, 0.2 g) together with B₂Pin₂ (1.15 mmol, 0.292 g), AcOK (2.6 mmol, 0.254 g), Pd(PPh₃)₂Cl₂ (0.052 mmol, 0.0365 g) and 1,4-dioxane (10 mL) was added into a 25 mL RBF under N₂. The resulting mixture was stirred for 10 min at r.t. and then the resulting mixture was stirred at 80° C. for 2 days. The mixture was diluted with water (30 mL), extracted by ethyl acetate (3×30 mL). The organic layer was dried over Na₂SO₄ and concentrated in vacuo. The resulting residue was purified by silica gel column chromatography to give the dioxaborolane product (0.1 g). ¹H NMR (400 MHz, CDCl₃): 9.60 (1H, d, J=4.0 Hz), 8.92 (1H, d, J=4.0 Hz), 8.21 (2H, d, J=12.0 Hz), 7.97 (2H, d, J=8.0 Hz), 7.88 (1H, d, J=8.0 Hz), 7.52 (1H, d, J=2.0 Hz), 7.32 (1H, dd, $J_1$=8.0 Hz, $J_2$=4.0 Hz), 4.02 (3H, s), 1.38 (12H, s).

Examples 5, 6, 8 and 9

Tin (II) chloride dihydrate (9.026 g, 40.0 mmol) was added to a solution of 4-bromo-2-nitrobenzaldehyde (2.3 g, 10.0 mmol) and EtOH (40 ml) followed by 3,3-diethoxypropionic acid ethyl ester (4.75 g, 25.0 mmol). The reaction was heated to 90° C. for 4 hr upon the cooling, the reaction mixture was concentrated and the residue was dissolved in EtOAc and quenched with sat. NaHCO$_3$. The resulting emulsion was filtered through a pad of celite and rinsed well with EtOAc. The remaining aqueous layer was extracted with EtOAc and the combined organic layer were washed with brine, dried over Na$_2$SO$_4$ and concentrated. The crude product was purified by silica gel column chromatography with 10-30% of EtOAc in hexanes to give ethyl 7-bromoquinoline-3-carboxylate (0.6 g, 21.5%). $\delta_H$ (400 MHz; CDCl$_3$) 1.47 (3H, t, J=8.0 Hz), 4.50 (2H, q, J=8.0 Hz), 7.72 (1H, t, J=4.0 Hz), 7.80 (1H, s), 8.36 (1H,$), 8.82 (1H, s), 9.45 (1H, s). $\delta_C$ (100 MHz; CDCl$_3$) 14.3, 61.7, 123.5, 125.4, 126.3, 130.2, 131.1, 138.5, 150.2, 151.0, 165.0.

Ethyl 7-bromoquinoline-3-carboxylate (0.526 g, 1.88 mmol), LiOH (0.45 g, 18.8 mmol) were added into a 25 mL round bottom flask. A mixed solvent THF/H$_2$O (2:1, 10 ml THF, 5 mL H$_2$O) was added and the reaction mixture was stirred at rt overnight. After acidified by 2M HCl. The precipitate was filtered and dried to afford 7-bromoquinoline-3-carboxylic acid (0.45 g, 95%). $\delta_H$ (400 MHz; d$_6$-DMSO) 7.86, 7.88 (1H, dd, $J_1$=8 Hz, $J_2$=2.0 Hz), 8.18 (1H, d, J=8.0 Hz), 8.32 (1H, d, J=2.0 Hz), 9.01 (1H, d, J=4.0 Hz), 9.31 (1H, d, J=4.0 Hz). $\delta_C$ (100 MHz; d$_6$-DMSO) 124.5, 125.9, 131.1, 131.9, 139.1, 150.0, 151.4, 166.5.

7-Bromoquinoline-3-carboxylic acid (0.252 g, 1.0 mmol) and CDI (0.204 g, 1.2 mmol) were dissolved in 10 mL DMF and stirred at room temperature for 30 min. ethyl 4-(amino (hydroxyamino)methyl)benzoate (0.2496 g, 1.2 mmol) was added and the reaction mixture was heated under reflux for about 24 hr. The mixture was poured into water (30 mL) and extracted with EtOAc (3×10 mL) and organic layer was dried over Na$_2$SO$_4$, filtered and concentrated in vacuo. The crude product was purified by silica gel to give ethyl 4-(5-(7-bromoquinolin-3-yl)-1,2,4-oxadiazol-3-yl)benzoate (Example 5) (0.35 g, 83%). $\delta_H$ (400 MHz; CDCl$_3$) 1.44 (3H, t, J=4.0 Hz), 4.44 (2H, q, J=8.0 Hz), 7.79 (1H, dd, $J_1$=8 Hz, $J_2$=2.0 Hz), 7.89 (1H, d, J=8.0 Hz), 8.20 (2H, d, J=8.0 Hz), 8.29 (2H, d, J=8.0 Hz), 8.41 (1H, d, J=4.0 Hz), 9.0 (1H, d, J=4.0 Hz), 9.67 (1H, d, J=2.0 Hz). $\delta_C$ (100 MHz; CDCl$_3$) 14.3, 61.4, 117.7, 125.5, 127.5, 130.1, 131.8, 136.3, 149.2, 150.0, 165.9, 168.6, 173.9, 176.1.

Ethyl 4-(5-(7-bromoquinolin-3-yl)-1,2,4-oxadiazol-3-yl) benzoate (5) (0.212 g, 0.5 mmol) together with B$_2$Pin$_2$ (0.254 g, 1.0 mmol), AcOK (0.245 g, 2.5 mmol), Pd(dppf) Cl$_2$ (0.037 g, 0.05 mmol) and 1,4-dioxane (10 mL) was added to a 25 mL round bottom flask under N$_2$. The resulting mixture was stirred at rt for 10 min, then heated at 90° C. for about 24 hr under N$_2$. After the reaction was complete, the reaction mixture was poured into 20 mL of H$_2$O and extracted by EtOAc. The combined organic layer was dried over Na$_2$SO$_4$, filtered and concentrated in vacuum. The crude product was purified by silica gel to give ethyl 4-(5-(7-(4,4,5,5-tetramethyl-1,3,2-dioxaborolan-2-yl) quinolin-3-yl)-1,2,4-oxadiazol-3-yl)benzoate (Example 8) (0.16 g, 68%). $\delta_H$(400 MHz; CDCl$_3$) 1.43 (15H, m), 4.43 (2H, q, J=8.0 Hz), 8.0 (2H, q, J=8.0 Hz), 8.21 (2H, d, J=12.0 Hz), 8.30 (2H, d, J=8.0 Hz), 8.70 (1H, s), 9.01 (1H, d, J=4.0 Hz), 9.69 (1H, d, J=2.0 Hz). $\delta_C$ (100 MHz; CDCl$_3$) 14.3, 24.9, 61.4, 84.4, 117.8, 127.5, 127.9, 128.4, 130.1, 136.3, 137.3, 148.2, 149.1, 165.9, 168.5, 174.2.

Ethyl 4-(5-(7-(4,4,5,5-tetramethyl-1,3,2-dioxaborolan-2-yl) quinolin-3-yl)-1,2,4-oxadiazol-3-yl)benzoate (8) (0.11 g, 0.23 mmol) and LiOH (0.056 g, 2.3 mmol) were added into a 25 mL round bottom flask, a mixed solvent THF/H$_2$O (4 ml:2 ml) was added and the reaction mixture was stirred at rt overnight. After acidified by 2.0M HCl, the reaction mixture was extracted by EtOAc, the combined organic layer were dried over Na$_2$SO$_4$, filtered and concentrated in vacuo. The residue was purified by recrystallization. The crude product was dissolved in acetone and precipitated out by adding diethyl ether, filtered and dried to afford 4-(5-(7-(4,4,5,5-tetramethyl-1,3,2-dioxaborolan-2-yl) quinolin-3-yl)-1,2,4-oxadiazol-3-yl)benzoic acid (Example 6) (0.097 g, 95%). $\delta_H$(400 MHz; d$_6$-DMSO) 1.34 (12H, s), 7.91 (1H, d, J=8.0 Hz), 8.15 (2H, d, J=8.0 Hz), 8.24 (3H, m), 8.39 (1H, s), 9.30 (1H, s), 9.56 (1H, d, J=4.0 Hz). $\delta_C$ (100 MHz; d$_6$-DMSO) 25.1, 84.8, 118.1, 127.9, 128.7, 129.4, 130.1, 130.7, 132.4, 137.3, 148.6, 167.0, 168.3, 174.6

4-(5-(7-(4,4,5,5-tetramethyl-1,3,2-dioxaborolan-2-yl) quinolin-3-yl)-1,2,4-oxadiazol-3-yl)benzoic acid (6) (0.09 g, 0.2 mmol) was dissolved in a mixed solvent of MeOH/H$_2$O (1:1), and then 1.0 M of HCl was added dropwise into the reaction mixture until pH=2. The resulting precipitate was filtered and dried under vacuum to provide 4-(5-(7-boronoquinolin-3-yl)-1,2,4-oxadiazol-3-yl)benzoic acid (Example 9) (0.07 g, 96%). δH (400 MHz; d$_6$-DMSO) 8.06 (1H, d, J=8.0 Hz), 8.22 (5H, m), 8.59 (1H, s), 9.25 (1H, s), 9.55 (1H, s). δC (100 MHz; d$_6$-DMSO) 117.5, 127.9, 128.6, 130.2, 130.7, 133.0, 137.1, 148.1, 148.9, 167.0, 168.2, 174.8.

Using a combined systems biology and experimental approach, we have previously identified homeodomain interacting protein kinase 2 (HIPK2) as a critical regulator of multiple pro-fibrosis pathways including TGF-β1/Smad3 pathway. HIPK2 regulates the pathway by physical association with Smad3, which thereby modulates its activity. Knockdown of HIPK2 in human primary tubular cells suppresses activation of the TGF-β1/Smad3 pathway induced by TGF-β1. In vivo, HIPK2 knockout inhibits TGF-β1/Smad3 activity and kidney fibrosis in both HIV1-transgenic mice (Tg26) and mice with unilateral ureteral obstruction (UUO). Suppression of TGF-β1/Smad3 pathway through inhibition of HIPK2, therefore provides an approach to anti-fibrosis therapy for kidney disease.

HIPK2 inhibitors have not been well developed and are not commercially available. Recently Cozza et al [PLoS One, 9: e89176, 2014] described a selective HIPK2 inhibitor that competes for the ATP binding in the kinase domain. However, since HIPK2 regulates multiple signaling pathways, including regulation of p53, there is a concern that broad inhibition of HIPK2 may not be beneficial in all cellular contexts. Here we describe compounds identified using a Smad3 reporter assay, that are able to inhibit TGF-β1/Smad3 pathway through the interruption of HIPK2-Smad3 protein-protein interaction without significant inhibition of HIPK2 kinase activity nor inhibition of p53 activation. In the tests shown below, Example 1 inhibited the pro-fibrosis pathway in vitro in cultured human renal tubular epithelial cells (RTEC) and in vivo in murine models of kidney fibrosis (Tg26 and UUO mice).

HEK 293T (293T) cells (ATCC) were cultured in Dulbecco's Modified Eagle's medium (Invitrogen) containing 10% fetal bovine serum (FBS), 0.5% penicillin and streptomycin at 37° C. and 5% CO$_2$ humidified environment. Human primary tubular cells (PromoCell GmbH, Heidelberg, Germany) were cultured in Renal Epithelial Cell Growth Medium-2 (Promocell GmbH) with supplements according to manufacturer's protocol human primary renal tubular epithelial cells with <5 passages were used for all studies. For HIV infection of hRTECs, pNL4-3:ΔG/P-EGFP, a gag/poi-deleted HIV-1 construct that contains EGFP in the gag open reading frame, and pHR-IRES-EGFP, a control EGFP construct, were used to generate the VSV-G pseudotyped virus. Cells were infected with HIV pseudotyped virus or control virus for 2 days before the treatment with test compound.

4×Smad binding element-driven firefly luciferase (SBE4-Luc) plasmid was purchased from Addgene (#16495). Renilla luciferase reporter plasmid (pRL) was purchased from Promega. Active domain deleted HIPK2 was previously described by Jin et al. [Nat Med, 18: 580-588]. The $His_6$-HIPK2 construct was generated by PCR amplification of coding region using plasmid containing human HIPK2 gene (GeneCopoeia™) as the template.

293T cells seeded in 12-well plate (~60% confluence) were co-transfected with SBE4-Luc (0.5 µg) and pRL plasmids (0.2 µg) using the PolyJet transfection kit according to manufacturer's instructions (SignaGen Laboratories, MD). Forty-eight hours post-transfection cells were treated with assigned concentrations of test compound together with or without 10 ng/ml TGF-β1 for 16 hours. Luciferase activities were measured using the Dual-Luciferase Reporter Assay kit (Promega, #E1910). Data are expressed as the ratio of firefly luciferase activity over Renilla luciferase activity. For HIPK2 dominant negative experiment, together with SBE4-firefly luciferase and pRL (Renilla luciferase) plasmids, either pcDNA 3.1 empty vector (0.5 µg) or HIPK2 KD plasmid (0.5 µg) was co-transfected into 293T cells. 48 hours after transfection, luciferase activities were measured.

Medium LDH measurement was performed using LDH Cytotoxicity Assay Kit (ThermoFisher scientific, NY) according to manufacturer's instructions.

HIPK2 kinase assay was performed by ProQinase GmbH (Freiburg, Germany).

Total RNA was extracted using Trizol (Invitrogen). 400 ng of total RNA was reverse transcribed to cDNA using SuperScript III first strand synthesis system (Invitrogen).

Quantitative RT-PCR was performed using 7500 Real-Time PCR System (Applied Biosystems). Gene level was normalized to glyceraldehyde 3-phosphate dehydrogenase (GAPDH) and expressed as fold change. The primer sets used were as follows:

```
human collagen I
(forward: 5'-CTCCCCAGCTGTCTTATGGC-3' (SEQ ID NO:

1);

reverse: 5'-GACCCATGGGACCTGAAGG-3' (SEQ ID NO: 2);

CTGF
(forward: 5'-CTTCTGTGACTTCGGCTCCC-3' (SEQ ID

NO: 3);

reverse: 5'-CTGGTACTTGCAGCTGCTCT-3' (SEQ ID NO:

4));

fibronectin 1
(forward: 5'-TGCAGTGGCTGAAGACACAA-3' (SEQ ID NO:

5);

reverse: 5'-ACGTCCTGCCATTGTAGGTG-3' (SEQ ID NO:

6));

MMP2
(forward: 5'-CCTGCAAGTTTCCATTCCGC-3' (SEQ ID NO:

7);

reverse: 5'-GTGAAGGGGAAGACACAGGG-3' (SEQ ID NO:

8));

PAI1
(forward: 5'-ATCAGCCACTGGAAAGGCAA-3' (SEQ ID NO:

9);

reverse: 5'-CTCTAGGGGCTTCCTGAGGT-3' (SEQ ID NO:

10));

α-SMA
(forward: 5'-GTATGTGGCTATCCAGCCGG-3' (SEQ ID NO:

11);

reverse: 5'-AATAGCCACGCTCAGTCAGG-3' (SEQ ID NO:

12));

GAPDH
(forward: 5'-AATTGAGCCCGCAGCCTCCC-3' (SEQ ID NO:

13);

reverse: 5'-CCAGGCGCCCAATACGACCA-3' (SEQ ID NO:

14)).
```

293T cells were lysed in equilibration/wash buffer (50 mM sodium phosphate, 300 mM sodium chloride, 10 mM imidazole; pH 7.4) 48 hours after transfection of $His_6$-tagged HIPK2 expression plasmid. Cleared cell lysate was incubated with HisPur Cobalt resin (Thermo Fisher Scientific, NY) on end-over-end rotator at 4° C. for 2 hours. After centrifugation (700×g, 2 min, 4° C.), the resin was washed 3 times in a wash buffer. The bound protein complexes were finally eluted with elution buffer (50 mM sodium phosphate, 500 mM sodium chloride, 150 mM imidazole; pH 7.4) and subjected to western blot analysis.

Cells were lysed in M-PER mammalian protein extraction reagent (#78501, Thermo Fisher Scientific, NY) containing protease inhibitor cocktail (#11836153001, Roche) and phosphatase inhibitors (50 mM NaF, 10 mM β-glycerophosphate, 5 mM sodium pyrophosphate, 2 mM $Na_3VO_4$). Total protein concentration was measured using the Bradford reagent (#500-0006, Bio-Rad). Proteins were separated on SDA-PAGE and transferred to nitrocellulose membrane. Immunoblotting was performed using specific antibodies: phospho-Smad3 (#9520, Cell Signaling), total Smad3 (#9523, Cell Signaling), 6×His (#ab137839, Abcam), HIPK2, (#5091, Cell Signaling), GAPDH (#2118, Cell Signaling), and α-SMA (#ab5694, Abcam).

Drug affinity responsive target stability (DARTS) method was used to identify protein targets of test compound as described previously by Pai et al. [Methods Mol Biol, 1263: 287-298, 2015]. Briefly, 293T lysates were incubated with test compound at room temperature for 1 hour. After incubation, cell lysates were subjected to proteolysis with various concentrations of pronase (#10165921001, Roche) at room temperature for 20 minutes. Proteolysis was stopped by addition of 5× protein loading buffer and heating at 90° C. for 5 minutes. Protein samples were subjected to western blot analysis.

Tg26 mice of FVB/N genetic background bearing a defective HIV-1 provirus lacking gag-pol have been described by Feng et al. [*J Am Soc Nephrol* 2009; 20: 2138-2146]. Six-week old heterozygous Tg26 mice were used in this study. Wildtype littermates were used as controls. Mice in the treatment group received test compound dissolved in DMSO and diluted in saline (5% DMSO) by oral gavage at a dose of 200 μg/kg body weight per day. Mice in the control group received the same volume of 5% DMSO/saline vehicle. The mice were treated for a total of 4 weeks and sacrificed at age of 10 weeks. The UUO model was established in male C57BL/6 mice (The Jackson Laboratory) by ligation of the left ureter as described by Jin et al. [Lab Invest, 93: 801-811, 2013]. After the operation, UUO mice were randomly divided into control group (vehicle) and treatment group. Mice were fed with test compound by oral gavage at a dose of 200 μg/kg body weight per day for 7 days.

Immunofluorescence staining was conducted on paraffin-embedded kidney sections using standard procedures. Briefly, deparaffinized sections were incubated with primary antibody against collagen I (1:50, #NB6-00-4-8, Novus) at 4° C. overnight. After being washed, sections were incubated with Alexa Fluor488-labelled second antibody (1:200, #A11034, Invitrogen) at room temperature for 1 hour in darkness. After nuclei were stained with 4', 6-diamidino-2-phenyllindole (DAPI) slides were mounted using Aqua PolyMount (Polysciences, Inc) and images were acquired using AxioVision IIe microscope with a digital camera.

Renal fibrosis was evaluated histologically by Sirius red staining on paraffin slides of mice kidney tissues according to the manufacturer's instructions (#ab150681, Abcam). Masson's trichrome staining on paraffin slices of mice kidney tissue was performed according to manufacturer's instructions (#87019, Thermo Scientific).

Data are reported as mean±SEM. The ANOVA followed by Bonferroni correction was used for comparison between groups. GraphPad Prism software was used for statistical analyses. All experiments were repeated at least three times, and representative experiments are shown. Data were considered statistical significant when $p<0.05$.

Results

Since Smad3 is a major downstream transcription factor activated by HIPK2 and an important mediator of renal fibrosis, the activity of test compounds was initially screened by a Smad3-responsive luciferase reporter (SBE4-Luc, containing a firefly luciferase gene under the control of multimerized Smad binding element) in HEK 293T cells. The results are shown in Table 1.

TABLE 1

| Example | Luciferase Activity (Relative to DMSO control) | |
|---|---|---|
| | −TGFβ | +TGFβ |
| DMSO | 1.000 | 2.520 |
| 1 | 0.197 | 0.457 |
| 2 | 0.660 | 0.935 |
| 3 | 0.730 | 1.318 |
| 4 | 0.366 | 0.508 |
| 5 | 0.512 | 0.494 |
| 6 | 0.722 | 2.284 |
| 7 | 0.784 | 2.355 |
| 8 | 0.818 | 4.451 |

To further confirm the inhibitory effect of compounds of the invention on Smad3 activity, the dose effect of a test compound on the SBE4-luciferase activity at a range of concentrations was determined. In the absence of TGF-β1 stimulation, Example 1 at increasing doses (3.3 μm and 10 μm) induced a progressive and significant suppression of Smad3 reporter activity (~40% and 70% inhibition compared to DMSO control, respectively). In the presence of TGF-β1, the SBE4-luciferase activity enhanced remarkably but it was significantly inhibited by Example 1 at all three tested doses (~40%, 60% and 75%, inhibition compared to TGFβ1-treated only control, respectively).

In order to rule out the possibility that the reduction in Smad3 activity is due to the cytotoxicity of increasing concentration of compound, lactate dehydrogenase (LDH) level in cell culture medium was examined. LDH is released by damaged cells. Even up to 30 μM of Example 1 for 16 hours of incubation no significant increase of LDH level in the culture medium was observed, suggesting that the repression of Smad3 activity by Example 1 is not due to cytotoxicity and cell death.

Since compounds of the invention attenuated the Smad3 activity, we examined the inhibition of HIPK2 kinase activity. Kinase assay was performed by ProQinase GmbH (Freiburg, Germany). No inhibition of HIPK2 kinase activity with increasing concentrations of Example 1 was observed, while staurosporine tested as an internal control in parallel showed an $IC_{50}$ of $4.7 \times 10^{-06}$ M. This result indicated that the decreased Smad3 activity upon administration of compounds of the invention was not dependent on the alteration of the kinase function of HIPK2. However, the question remained whether HIPK2 activity is nevertheless required for Smad3 activation. We employed the kinase-dead HIPK2 (KD-HIPK2) expression in 293T cells, which serves as a dominant negative mutant to inhibit the endogenous HIPK2 activity. We found that overexpression of KD-HIPK2 significantly suppressed SBE4-luciferase reporter activity in 293T cells treated with TGF-β1 as compared to cells transfected with a wildtype HIPK2 (WT-HIPK2). These data further confirm that the inhibition of HIPK2 kinase activity suppresses TGF-β1-induced Smad3 phosphorylation. In addition, an additive inhibitory effect between Example 1 and overexpression of KD-HIPK2 on Smad3 activity was observed. Together with the results of the kinase assay, the data indicated that the binding of Example 1 on HIPK2—leading to repression of Smad3 activity—is through a mechanism other than the inhibition of HIPK2 kinase activity.

Since Example 1 did not affect kinase activity of HIPK2, we sought to determine whether it physically binds to HIPK2 to alter its effects on Smad3 activity, since it is known that steric or allosteric binding of compounds to target proteins can change their activity, functioning as either activators or inhibitors. Drug affinity responsive target stability (DARTS) has recently been developed to identify potential protein targets of small molecules. It is based on the principle that the binding of small molecule compound to the target protein changes the protein structure such that it can increase its stability and confer protection against proteolysis. In order to test whether compounds of the invention bind directly to HIPK2, we performed the DARTS experiments using pronase in presence of Example 1. Upon digestion with a serial dilution of pronase to cell lysate concentration ratio, we found that HIPK2 was protected from degradation at 1:10,000 pronase/cell lysate ratio in presence of Example 1, but not in the presence of DMSO control. To further confirm this result, we examined dose effects of Example 1 on protection of HIPK2 from pronase digestion. At the same 1:10,000 pronase/cell lysate ratio, we found that a partial protection was observed at 30 µm of Example 1 and a complete protection at 100 µm, confirming that Example 1 physically bound to HIPK2. Since it is known that HIPK2 interacts with Smad3, and this study showed that the physical binding of Example 1 to HIPK2 represses Smad3 activation, it appears that the binding of compounds of the invention to HIPK2 alters the protein-protein interaction between HIPK2 and Smad3. Because HIPK2 abundance is quite low in many known cell types, we overexpressed His6-tagged HIPK2 in 293T cells for testing its interaction with the endogenous Smad3. The expression of His6-HIPK2 and Smad3 in 293T cells was confirmed by western blot. We pulled down His6-HIPK2 using cobalt beads and checked for the presence of Smad3 in cells treated with two different doses of Example 1. Example 1 indeed reduced the interaction between Smad3 and HIPK2 in a dose-dependent manner, suggesting that binding of the compounds of the invention to HIPK2 interferes with its interaction with Smad3.

The effects of compounds of the invention on Smad3 phosphorylation and the expression of the downstream target genes of TGF-β/Smad3 pathway was also examined. Stimulation of primary human renal tubular epithelial cells (hRTECs) with TGF-β1 (5 ng/ml) for 20 minutes resulted in robust phosphorylation of Smad3. However, Smad3 phosphorylation induced by TGF-β1 was gradually inhibited by pretreatment of cells with Example 1 in a dose dependent manner. The expression levels of TGF-β1/Smad3 downstream target genes, such as Col I, CTGF, FN1, MMP2, PAI1 and α-SMA, was examined by real-time PCR. In the absence of TGF-β1 stimulation, pretreatment of Example 1 did not affect expression of these genes. Treatment of cells with TGF-β1 remarkably increased the expression of these genes, which was progressively inhibited by pretreatment with increasing concentrations of Example 1. Taken together, these data further support an inhibitory effect of compounds of the invention on TGF-β1/Smad3 pathway.

TGF-β1/Smad3 pathways are key regulators of pro-fibrosis pathway in kidney disease, and the in vitro data above indicate that compounds of the invention inhibit the expression of pro-fibrosis genes. The unilateral ureteral obstruction (UUO) mouse model, a commonly used model for renal fibrosis, was used to determine whether compounds of the invention can ameliorate fibrosis in vivo. We treated both UUO and sham-operated mice with either Example 1 at 200 µg/kg body weight/day or DMSO as vehicle control by daily oral gavage from the day of the surgery to 7 days post-surgery. The fibrosis was observed by picrosirius red staining, Masson's trichrome staining, and immunofluorescence staining of Collagen I. Treatment with Example 1 significantly attenuated renal fibrosis in the UUO mice as compared to vehicle-treated UUO mice. Western blot of the kidney cortex lysates showed that the treatment with Example 1 significantly decreased Smad3 phosphorylation and α-SMA expression in the UUO kidneys, further supporting that the attenuation of the fibrotic response is mediated by the inhibition of HIPK2/Smad3 pathway.

In addition, administration of Example I starting at day 7 post-surgery (day 7 to 14) that allowed for onset of fibrosis to commence in UUO mice prior to treatment also showed efficacy in amelioration of fibrosis progression. Similar to early treatment, despite starting 7 days post-surgery BT173 administration led to a significant attenuation of fibrosis at 14 days post-surgery, as observed by picrosirius red staining, Masson's trichrome staining, and immunofluorescence staining of Collagen I. Western blot of kidney cortex showed a marked reduction in p-Smad3 and α-SMA in Example 1-treated UUO kidneys in comparison to vehicle-treated UUO kidneys. Although p53 phosphorylation was significantly elevated in UUO kidneys in comparison to sham-operated kidneys, Example 1 had no effects on p53 activation, consistent with the above in vitro findings. In addition, real-time PCR analysis revealed a significant upregulation of genes in the Wnt/β-catenin pathway (Axin2, c-myc, and Twist) in UUO kidneys in comparison to sham-operated. Example 1-treatment also significantly diminished their expressions, further corroborating the above in vitro demonstration of Example 1's effect on HIPK2 to suppress the activation of the Wnt pathway induced in the injured kidney.

Since the utility of the UUO model is limited to renal fibrosis, and it does not allow for examination of the renal function, we employed a second mouse model of renal fibrosis. Tg26 mice are known to develop proteinuria starting from 4 weeks of age and the proteinuria peaks usually around 8-10 weeks of age. Tg26 mice also develop significant glomerulosclerosis and renal failure by 8-10 weeks of age. To determine whether compounds of the invention could reverse kidney injury that has been already developed, we started to treat Tg26 mice with either vehicle or Example 1 from age of 6 weeks for a total of 4 weeks, and the mice were sacrificed at age of 10 weeks. We found that Example 1 significantly reduced proteinuria and improved renal function in Tg26 mice compared to mice treated with vehicle, as shown in Table 2 and Table 3.

TABLE 2

| | Urinary Albumin:Creatinine Ratio (µg/µg) | | | |
|---|---|---|---|---|
| | Wildtype + vehicle | Wildtype + Example 1 | Tg26 + Vehicle | Tg26 + Example 1 |
| Pre-treatment (week 0) | 0.038 ± 0.006 | 0.033 ± 0.007 | 28.427 ± 7.931 | 23.321 ± 12.339 |
| Post-treatment (week 4) | 0.044 ± 0.026 | 0.036 ± 0.008 | 46.910 ± 15.853 | 19.917 ± 5.838 |

TABLE 3

| | BUN (mg/dL) | | | |
|---|---|---|---|---|
| | Wildtype + vehicle | Wildtype + Example 1 | Tg26 + Vehicle | Tg26 + Example 1 |
| Pre-treatment (week 0) | 17.972 ± 3.312 | 21.091 ± 3.009 | 21.255 ± 4.975 | 23.799 ± 1.990 |
| Post-treatment (week 4) | 20.188 ± 4.560 | 18.875 ± 3.485 | 51.784 ± 5.407 | 22.404 ± 4.678 |

Example 1 also attenuated kidney injury and renal fibrosis in Tg26 mice as shown by picrosirius red staining, Masson's trichrome staining, and immunofluorescence of Collagen I. In addition, Example 1 significantly reduced Smad3 phosphorylation and α-SMA expression in Tg26 mice.

---

What is claimed is:

1. A compound of formula I

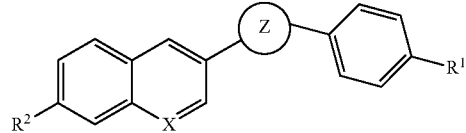

wherein

Z is an oxadiazole;

X is N;

$R^1$ and $R^2$ are chosen independently from —($C_1$-$C_8$) hydrocarbyl, OH, —O($C_1$-$C_8$)hydrocarbyl, halogen, nitro, ($C_1$-$C_3$)alkylamino, ($C_1$-$C_3$)dialkylamino, ($C_1$-$C_3$)acylamino, ($C_1$-$C_3$)alkylsulfonyl, ($C_1$-$C_3$)alkylthio, ($C_1$-$C_3$)haloalkyl, ($C_1$-$C_3$)haloalkoxy, ($C_1$-$C_3$)haloalkylthio, —COOH, —C(=O)O($C_1$-$C_3$)alkyl, —B($OR^3$)$_2$, and —$BF_3$K; and $R^3$ is H or ($C_1$-$C_8$)hydrocarbyl; or ($OR^3$)$_2$, taken together with the boron to which they are attached form a dioxaborolane or dioxaborinane ring optionally substituted with from one to four ($C_1$-$C_8$)hydrocarbyl.

2. A compound according to claim 1 wherein Z is

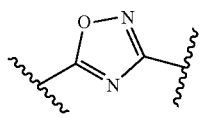

3. A compound according to claim 1 wherein Z is

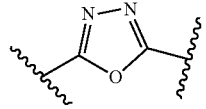

4. A compound according to claim 1 wherein $R^1$ is chosen from halogen, —COOH, —C(=O)O($C_1$-$C_3$)alkyl, —B($OR^3$)$_2$, and —$BF_3$K.

5. A compound according to claim 1 wherein $R^2$ is chosen from halogen, ($C_1$-$C_3$)haloalkyl, —O($C_1$-$C_3$)alkyl, —B($OR^3$)$_2$, and —$BF_3$K.

6. A compound according to claim 1 wherein $R^1$ is chosen from bromine, COOEt, and —$BF_3$K.

7. A compound according to claim 1 wherein $R^2$ is chosen from bromine, $CF_3$ and —$OCH_3$.

8. A pharmaceutical composition comprising a pharmaceutically acceptable carrier and a compound according to claim 1.

9. A method for inhibiting the interaction of homeodomain interacting protein kinase 2 (HIPK2) with Smad3, said method comprising bringing HIPK2 into contact with a compound of claim 1.

10. A method for inhibiting Smad3 activation, said method comprising bringing Smad3 into contact with a compound of claim 1.

11. The method according to claim 9 wherein the method is an in vitro method.

12. The method according to claim 9 wherein the method is an in vivo method.

13. The method according to claim 10 wherein the method is an vitro method.

14. The method according to claim 10 wherein the method is an in vivo method.

15. A method for treating a fibrotic disease comprising administering a compound of claim 1 to a subject suffering from a fibrotic disease.

16. A method according to claim 15 wherein said disease is renal fibrosis.

17. A compound of formula II

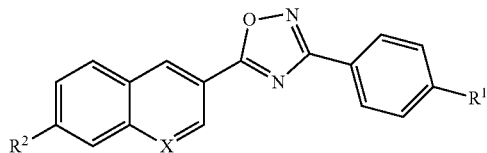

II wherein

X is chosen from N and CH;

$R^1$ and $R^2$ are chosen independently from —($C_1$-$C_8$)hydrocarbyl, OH, —O($C_1$-$C_8$)hydrocarbyl, halogen, nitro, ($C_1$-$C_3$)alkylamino, ($C_1$-$C_3$)dialkylamino, ($C_1$-$C_3$)acylamino, ($C_1$-$C_3$)alkylsulfonyl, ($C_1$-$C_3$)alkylthio, ($C_1$-$C_3$)haloalkyl, ($C_1$-$C_3$)haloalkoxy, ($C_1$-$C_3$)haloalkylthio, —COON, —C(=O)O($C_1$-$C_3$)alkyl, —B(O$R^3$)$_2$, and —BF3K; and $R^3$ is H or ($C_1$-$C_8$)hydrocarbyl; or (O$R^3$)$_2$, taken together with the boron to which they are attached form a dioxaborolane or dioxaborinane ring optionally substituted with from one to four ($C_1$-$C_8$)hydrocarbyl, with the provision that when X is CH and $R^2$ is —O($C_1$-$C_3$)alkyl, then $R^1$ is not ($C_1$-$C_3$)alkyl.

18. A method for inhibiting the interaction of homeodomain interacting protein kinase 2 (HIPK2) with Smad3, said method comprising bringing HIPK2 into contact with a compound of claim 17.

19. A method for inhibiting Smad3 activation, said method comprising bringing Smad3 into contact with a compound of claim 17.

20. A method for treating a fibrotic disease comprising administering a compound of claim 17 to a subject suffering from a fibrotic disease.

21. A method according to claim 20 wherein said disease is renal fibrosis.

* * * * *

UNITED STATES PATENT AND TRADEMARK OFFICE
CERTIFICATE OF CORRECTION

PATENT NO. : 10,669,266 B2  
APPLICATION NO. : 16/473878  
DATED : June 2, 2020  
INVENTOR(S) : He et al.

Page 1 of 1

It is certified that error appears in the above-identified patent and that said Letters Patent is hereby corrected as shown below:

In the Claims

Column 28, Line 1: Claim 17, Delete "-COON," and insert -- -COOH, --

Signed and Sealed this  
Eighteenth Day of August, 2020

Andrei Iancu  
*Director of the United States Patent and Trademark Office*

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
ctccccagct gtcttatggc        20

<210> SEQ ID NO 2
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 2
gacccatggg acctgaagg         19

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
cttctgtgac ttcggctccc        20

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
ctggtacttg cagctgctct        20

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5

| | | |
|---|---|---|
| tgcagtggct gaagacacaa | | 20 |

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6

| | | |
|---|---|---|
| acgtcctgcc attgtaggtg | | 20 |

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7

| | | |
|---|---|---|
| cctgcaagtt tccattccgc | | 20 |

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8

| | | |
|---|---|---|
| gtgaagggga agacacaggg | | 20 |

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9

| | | |
|---|---|---|
| atcagccact ggaaaggcaa | | 20 |

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10

| | | |
|---|---|---|
| ctctaggggc ttcctgaggt | | 20 |

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11

| | | |
|---|---|---|
| gtatgtggct atccagccgg | | 20 |

<210> SEQ ID NO 12
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 12
aatagccacg ctcagtcagg                                                 20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
aattgagccc gcagcctccc                                                 20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
ccaggcgccc aatacgacca                                                 20
```